United States Patent [19]

Prokosch et al.

[11] 4,443,437

[45] Apr. 17, 1984

[54] VETERINARY COMPOSITION AND METHOD OF USING SAME

[76] Inventors: Walter G. Prokosch; Robert L. Marshall, both of Rte. 2, P.O. Box 65, Honey Grove, Tex. 75446

[21] Appl. No.: 422,363

[22] Filed: Sep. 23, 1982

[51] Int. Cl.³ .............................................. A61K 35/78
[52] U.S. Cl. ..................................................... 424/195
[58] Field of Search ................................ 424/195, 318

[56] References Cited
PUBLICATIONS

Cannon, Talloils:, Chem. Engineering, Jun. 1954, pp. 142–146.

Primary Examiner—Jerome D. Goldberg
Assistant Examiner—John W. Rollins, Jr.
Attorney, Agent, or Firm—Michael P. Breston

[57] ABSTRACT

This invention relates to a topical veterinary composition and a method of using same for the treatment of flesh wounds or lacerations or fistulas in animals and to promote the healing thereof. The composition comprises as the active ingredient tall oil either per se or as a topical veterinary ointment comprising the active ingredient in admixture with a suitable carrier and/or antiseptic.

10 Claims, No Drawings

VETERINARY COMPOSITION AND METHOD OF USING SAME

BACKGROUND OF THE INVENTION (1) Field of Invention

This invention relates to a veterinary composition and a method of using same. More particularly the invention concerns a topical veterinary composition for the treatment of flesh wounds or lacerations or fistulas in animals, to promote the healing thereof, and comprising as the active ingredient tall oil. In another aspect the invention concerns a method for treating flesh wounds, lacerations or fistulas in animals to promote the healing thereof and which comprises topically applying tall oil thereto either per se or as a topical veterinary ointment comprising the active ingredient in admixture with a suitable carrier and/or antiseptic.

(2) Description of the Prior Art

Fistulas are by definition pathological sinuses or abnormal passages leading from an abscess cavity or a hollow organ to the surface or from one abscessed cavity or a hollow organ to another. This invention concerns itself mainly with the topical treatment of lymphatic fistulas and lacerations. The majority of lymphatic fistulas in horses may be caused by, or result from abscesses, bruises, wounds or by long continued irritations. Fistulous withers and poll evil in horses and in ruminants may also be caused by brucella abortus infections. Horses with fistulous wither and positive serum agglutination tests are commonly treated by vaccination with Br. abortus. The surface of fistulas or lacerations should also be treated.

Veterinary agents for the treatment of flesh wounds and fistulas in animals to promote the healing thereof are known. One such agent is a topical wound spray (Blue wound lotion) comprising an aqueous solution of propylene glycol, methyl violet, neomycin sulfate, benzalkonium chloride and ethylene-diamine tetracetate. Another known wound treating agent comprises furazolidone as the active ingredient.

Whilst such agents are effective in many cases, they have been found to be less effective in certain cases, particularly in cases of severe wounding. A need therefore exists for an improved agent for promoting the healing of flesh wounds or fistulas in animals.

SUMMARY OF INVENTION

In accordance with the present invention it has been found that tall oil is an effective agent for the treatment of flesh wounds, lacerations and surface fistulas in animals to promote the healing thereof.

DETAILED DESCRIPTION

The invention is based on the discovery that tall oil is a very effective therapeutic agent in the treatment of flesh wounds, lacerations and fistulas in animals.

Tall oil is a by-product of the paper-making industry and is obtained by acidifying the black liquor skimmings resulting from the alkaline treatment of wood pulp, particularly in the sulfate (kraft) process of wood pulp manufacture.

Crude tall oil is essentially a mixture of rosin (e.g. abietic and pimaric) acids and fatty (primary oleic and linoleic, but also comprising small amounts of others such as palmitic, palmitoleic, stearic and other $C_{17}-C_{22}$ acids in isomeric or conjugated form) acids in approximately equal proportions plus a small proportion (e.g. up to about 10% by weight) of neutral material comprising primarily esters of fatty acids but containing small amounts of sterols, higher alcohols and hydrocarbons. The precise composition of tall oil will vary with the original wood source used to prepare the wood pulp and with the degree of refinement of the tall oil after acidification; thus the term tall oil used herein includes the acidic mixture obtained by the acidification of the black liquor resulting from the alkaline pulping of wood pulp from any source, and includes refined (i.e. distilled) tall oil as well as the crude product. Suitable tall oil products for use in the present invention are available from Union Camp (Chemical Division), Savannah, Ga., under the trademark UNITOL CX, from Sylvachem Corp. under the trademark SYLVEX, from Arizona Chemical Co. under the trademark ACTINOL FA, and from Georgia-Pacific Corporation.

The tall oil may be applied as such as a topical medicament directly to the wounded area of the animal as often as may be desired to promote healing, but usually one to three times a day for several days or until the wound is healed. More usually, however, for use in accordance with this invention the tall oil will be formulated as a topically administrable composition, i.e. as an ointment, powder, lotion, spray or aerosol, comprising the active ingredient in admixture with a suitable topically administrable carrier or diluent. Particularly suitable carriers or diluents which may be used in the compositions of this invention are low molecular weight alcohols, especially isopropanol or ethanol. Other suitable carriers or diluents will be apparent to those skilled in the art. The proportions of tall oil to carrier are in no way critical.

In addition to the active tall oil ingredient the compositions of this invention may contain minor proportions by weight of other active ingredients and particularly an antiseptic, such as camphor, or other veterinarologically acceptable antiseptic compounds.

A particularly preferred, but exemplary liniment solution in accordance with this invention comprises:

| Tall oil | 20–70% by weight |
| Alcohol (ethanol or isopropanol) | 10–60% by weight |
| Camphor | 5–20% by weight |

The invention is illustrated by the following Examples.

EXAMPLE 1

A number of fistulous horses were placed in stalls so as to be readily available for treatment and observation. Prior to treatment the fistulas were cleaned with soap and water, and any interfering hair removed. The fistulas were then sprayed three times a day for 14 days with a liniment solution comprising:

| Tall Oil | 20–70% by weight |
| Alcohol (ethanol or isopropanol) | 10–60% by weight |
| Camphor | 5–20% by weight |

Sufficient liniment was applied to thoroughly saturate the area of the fistula.

Noticeable healing was discerned on the second day of treatment, and by the fourteenth day healing was virtually complete.

EXAMPLE 2

After six weeks of unsuccessful treatment with known veterinary wound healing agents, a colt with a severe injury incurred eight weeks previously (sufficient in many eyes to require the animal to be destroyed) comenced a course of treatment with a liniment substantially as described in Example 1, and applied liberally to the wound once daily. After 7 days a considerable improvement was already noticeable and was maintained with a substantial reduction in area and severity of laceration and with a substantial regrowth of hair to the wounded area over the next 21 days.

EXAMPLE 3

A colt with a lacerated hind leg denuded of skin and tissue sufficient to expose the tendons and, in one area, approximately 2×10 cms of the third metatarsal was presented for treatment. Initial treatment over 5 days with a mixture of DMSO and furazolidone ointment showed no healing, nor did one week's subsequent treatment with a proprietary neomycin-containing spray.

Treatment was then commenced with a liniment substantially as described in Example 1 applied liberally as a spray twice daily to the wounded area. After two days, healing was already noticeable and at 2 weeks the wound was found to be granulated in. A hair growth was evident except in the area of the exposed region of the metatarsal. This area eventually granulated in and had substantially healed within approximately 2 more weeks of treatment.

EXAMPLE 4

A 6 month old cat which had been hit by a car was presented for treatment. The injury sustained was abrasion of the right hind leg with loss of skin on the lower leg from the tarsal area distally to the foot. Treatment commenced with a liniment as described in Example 1 applied liberally twice daily. After 6 days of treatment there was complete coverings of the lacerated area with beginning growth of new hair. Treatment was then terminated, and on inspection one week later it was hard to discern which leg had been injured.

The examples thus presented clearly demonstrate the effectiveness of tall oil as an agent for promoting and accelerating the healing of surface wounds, fistulas and lacerations in animals.

In so far as tall oil, i.e., mixtures of rosin (abietic and pimaric) acids and long chain fatty acids (oleic and linoleic), may be obtained from sources other than paper pulp manufacture, tall oil obtained from such alternative sources is suitable for use in the method and composition of this invention and is within the scope of the appended claims.

What we claim is:

1. A mehtod of treating wounds, lacerations or surface fistulas in animals to promote the healing thereof, which comprises topically applying an effective amount of tall oil to the affected area for promoting healing thereof.

2. A method according to claim 1, in which the tall oil is applied to the affected area in admixture with a veterinary acceptable diluent or carrier.

3. A method according to claim 2, in which the tall oil is applied as a liniment comprising the tall oil in solution in a carrier selected from the group consisting of ethanol and isopropanol.

4. A method according to claim 1, in which the affected area is treated with a liniment comprising, on a weight basis:

| Tall oil | 20–70% |
| --- | --- |
| Alcohol | 10–60% |
| Camphor | 5–20% | wherein the alcohol is selected from the group consisting of ethanol and isopropanol.

5. A topical veterinary composition for the treatment of wounds, lacerations and surface fistulas in animals to promote healing comprising an effective amount of tall oil in admixture with a veterinary acceptable topical carrier.

6. A topical composition according to claim 5, in which the carrier is a lower alcohol.

7. A topical composition according to claim 6, in which the carrier is selected from the group consisting of ethanol and isopropanol.

8. A topical composition according to claim 5, which also contains an effective amount of an antispetic.

9. A topical composition according to claim 8, in which the antiseptic is camphor.

10. A topical composition according to claim 5, which is a liniment comprising on a weight basis:

| Tall oil | 20–70% |
| --- | --- |
| Alcohol | 10–60% |
| Camphor | 5–20% | in which the alcohol is selected from the group consisting of ethanol and isopropanol.

* * * * *